(12) United States Patent
Chen et al.

(10) Patent No.: US 10,364,265 B1
(45) Date of Patent: Jul. 30, 2019

(54) ANHYDROSUGAR SYNTHESIS

(71) Applicant: William Marsh Rice Univeristy, Houston, TX (US)

(72) Inventors: Li Chen, Houston, TX (US); Michael S Wong, Houston, TX (US); Zongchao Zhang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 15/380,030

(22) Filed: Dec. 15, 2016

Related U.S. Application Data

(60) Provisional application No. 62/267,684, filed on Dec. 15, 2015.

(51) Int. Cl.
*C07H 3/10* (2006.01)

(52) U.S. Cl.
CPC .................................... *C07H 3/10* (2013.01)

(58) Field of Classification Search
None
See application file for complete search history.

(56) References Cited

U.S. PATENT DOCUMENTS

| | | |
|---|---|---|
| 1,437,615 A | 12/1922 | Pictet |
| 3,235,541 A | 2/1966 | Lewis |
| 3,309,356 A | 3/1967 | Arnulf |
| 3,374,222 A | 3/1968 | Peniston |
| 5,023,330 A | 6/1991 | Gander |
| 5,371,212 A | 12/1994 | Moens |
| 5,395,455 A | 3/1995 | Scott |
| 5,432,276 A | 7/1995 | Moens |
| 2010/0317879 A1 | 12/2010 | Zhao |

OTHER PUBLICATIONS

Branca, Energy Fuels 2012, 26, 1520-1530. (Year: 2012).*
Houminer, Israel Journal of Chemistry vol. 7, 1969, pp. 535-546. (Year: 1969).*
Al-Etaibi, Tetrahedron Letters 46 (2005) 31-35. (Year: 2005).*
Paulsen, Primary and Secondary Reactions of Cellulose Melt Pyrolysis, Fall 2014, University of Massachusetts—Amherst. (Year: 2014).*
Lu, Qiang et. al. 2011 "Selective fast pyrolysis of biomass impregnated with ZnCl2 to produce furfural: Analytical Py-Gc/MS study", Journal of Analytical and Applied Pyrolysis 90: 204-212.
Czernik, S, and AV Bridgewater. 2004. "Overview of Applications of Biomass Fast Pyrolysis Oil." Energy & Fuels, 590-98. http://pubs.acs.org/doi/abs/10.1021/ef034067u.
Deng, Weiping, Mi Liu, Qinghong Zhang, Xuesong Tan, and Ye Wang. 2010. "Acid-Catalysed Direct Transformation of Cellulose into Methyl Glucosides in Methanol at Moderate Temperatures." Chemical Communications (Cambridge, England) 46 (15): 2668-70. doi:10.1039/b925723c.
Mettler, Matthew S., Samir H. Mushrif, Alex D. Paulsen, Ashay D. Javadekar, Dionisios G. Vlachos, and Pual J. Dauenhauer. 2012. "Revealing Pyrolysis Chemistry for Biofuels Production: Conversion of Cellulose to Furans and Small Oxygenates." Energy & Environmental Science 5 (1): 5414. doi:10.1039/c1ee02743c.
Patwardhan, Pushkaraj R., Justinus a. Satrio, Robert C. Brown, and Brent H. Shanks. 2009. "Product Distribution from Fast Pyrolysis of Glucose-Based Carbohydrates." Journal of Analytical and Applied Pyrolysis 86 (2): 323-30. doi:10.1016/j.jaap.2009.08.007.
Radlein, D. 2002. "Study of Levoglucosan Production—A Review." In Fast Pyrolysis of Biomass: A Handbook, edited by AV Bridgwater, 205-41.
Yang, Yu, Mahdi M. Abu-Omar, and Changwei Hu. 2012. "Heteropolyacid Catalyzed Conversion of Fructose, Sucrose, and Inulin to 5-Ethoxymethylfurfural, a Liquid Biofuel Candidate." Applied Energy 99 (Nov.): 80-84. doi:10.1016/j.apenergy.2012.04.049.

\* cited by examiner

*Primary Examiner* — Layla D Berry
(74) *Attorney, Agent, or Firm* — Boulware & Valoir

(57) ABSTRACT

Improved methods of making anhydrosugars by pyrolysis of a substrate sugar to remove at least one water molecule thereby producing a desired anhydrosugar and side products, the improvement being either 1) protecting one hydroxyl group of the substrate sugar before pyrolysis; or (2) pretreating the substrate sugar with a metal salt and optional acid before pyrolysis, wherein lower amounts of said side products are produced by said improved method.

8 Claims, 9 Drawing Sheets

2% LGA selectivity

>90% LGA selectivity

ANHYDROSUGAR SYNTHESIS

PRIOR RELATED APPLICATIONS

This case claims priority to U.S. Ser. No. 62/267,684, filed Dec. 15, 2015, and incorporated by reference herein in its entirety for all purposes.

FEDERALLY SPONSORED RESEARCH STATEMENT

This invention was made with government support under CBET-1153232 awarded by the NSF. The government has certain rights in the invention.

FIELD OF THE DISCLOSURE

The inventions are new methods to produce anhydrosugars. Specifically, two-step and one-step conversions of carbohydrates to anhydrosugars, such as levoglucosan, are described.

BACKGROUND OF THE DISCLOSURE

Methods of dehydrating biomass-derived carbohydrate are important and attractive chemical reactions because they produce valuable anhydrosugar compounds from renewable sources. Anhydrosugars are sugar derivatives that formally arise by the elimination of one or more water molecules from arbitrary hydroxyl groups of the parent aldose or ketose derived from carbohydrates. They usually contain a bicyclic or tricyclic skeleton composed of oxirane, oxetane, oxolane (tetrahydrofuran), and oxane (tetrahydropyran) rings (e.g., levoglucosan, 1,6-anhydro-β-d-glucofuranose, levoglucosenone, 1,4:3,6-dianhydro-α-D-glucopyranose, mannosan, galactosan, etc.). They can also be compounds without bicyclic or tricyclic skeletons, such as 5-hydroxymethylfurfural, furfural, maltol, etc. Examples of anhydrosugars are shown in FIG. 1.

Carbohydrates, with pentose and hexose as the building blocks, include monosaccharides (e.g., pentose and hexose, and derivatives thereof), disaccharides (e.g., sucrose, maltose, lactose, cellobiose, and derivatives or byproducts thereof), and polysaccharides (e.g., maltodextrins, starches, cellulose, and derivatives or byproducts thereof). Any of these can be used as starting materials to make desired anhydrosugars.

For pentose sugars ($C_5H_{10}O_5$, e.g., arabinose, xylose, ribose, and lyxose), the corresponding dehydration products will have one of the following formulas: $C_5H_8O_4$, $C_5H_6O_3$, $C_5H_4O_2$, or $C_5H_2O$. For hexose ($C_6H_{12}O_6$, e.g., glucose, fructose, mannose, and galactose), the corresponding dehydration products will have one of the following formulas: $C_6H_{10}O_5$, $C_6H_8O_4$, $C_6H_6O_3$, or $C_6H_4O_2$.

Levoglucosan is one well-known anhydrosugar with uses as a raw material for production of pharmaceuticals (e.g., Avermectin), polymers and surfactants. For example, levoglucosan can be used to create SGLT2 inhibitors used in generic diabetes drugs. However, large-scale production of levoglucosan remains elusive due to the extensive purification steps required (Czernik and Bridgwater 2004). It has been known for many years that starch containing materials and cellulose, or lignocellulosic materials (e.g., wood), may be converted to levoglucosan by pyrolysis. But most researchers have identified the efficient isolation of levoglucosan from the pyrolytic liquids as the main difficulty in the efficient production of levoglucosan (Czernik and Bridgwater 2004; Radlein 2002).

If a simple, cheap and reliable method could be found for levoglucosan production, it would be an important breakthrough in this field. Thus, several processes have been patented for generation, recovery and purification of levoglucosan from pyrolysis of cellulose or lignocellulose.

In U.S. Pat. No. 1,437,615, for example, a batch vacuum pyrolysis process was described (pyrolysis temperature range is 200° C. to 300° C., pressure is 12-15 mm Hg). The starting substrate was cellulose, starch and sawdust. The pyrolysis products derived from carbohydrate materials were fractionally condensed, dehydrated and extracted into boiling acetone to get the crystallized levoglucosan. However, this "acetone method" used a volatile and flammable solvent.

In U.S. Pat. No. 3,309,356, azeotropic distillation and methyl isobutyl ketone extraction were combined to separate levoglucosan from pyrolyzed Douglas fir sawdust (pyrolysis temperature: 600-1500° F.). The crude products included: char, light gases, and condensable gases (e.g., tars, substituted phenolic materials, levoglucosan and carbohydrate derived acids).

U.S. Pat. No. 3,374,222 used the same substrate, pyrolysis condition and pyrolysis crude products as U.S. Pat. No. 3,309,356. Impurities, such as polymeric carbohydrate-derived acids, were precipitated by adding basic metal salts (e.g., alkaline earths, aluminum, lead or zinc). Levoglucosan was then crystallized from the concentrated filtrate.

In U.S. Pat. No. 3,235,541, a wood pulp containing 96% alpha-cellulose was used as the substrate. The pyrolysis temperature was 350° C., 400° C. and 450° C. The crude products included char, light gases and crude levoglucosan. This patent describes a process that used chloroform to remove the colored impurities in cellulose-derived pyrolysis oil in order to get high purity levoglucosan. However, chloroform is highly toxic.

In U.S. Pat. No. 5,395,455, partial oxidative pyrolysis processes were conducted using pyrolysis temperatures between 400° C. and 650° C. The substrate was either (1) commercial cellulose washed by 5% sulfuric acid, or (2) hybrid poplar wood which had been pre-hydrolyzed using 5% sulfuric acid. The pyrolysis crude products contained 35-51.4% anhydrosugars (e.g., levoglucosan, anhydroglucofuranose and cellobiosan). The aqueous phase from water induced phase separation of the pyrolysis products was first dewatered, then extracted by hot alcohol followed by charcoal treatment, then after solvent evaporation, the levoglucosan remained.

In U.S. Pat. No. 5,023,330, the pyrolysis products were condensed and neutralized with alkali to a pH of about 6 to 8. Then a chromatographic method was used to purify levoglucosan. The substrate was commercial starch and wheat flour, and the pyrolysis temperature was 200° C. to 500° C.

In U.S. Pat. Nos. 5,371,212 and 5,432,276, cellulose/starch/waste newsprint were washed with hot acid and pyrolyzed at a temperature of 350-375° C. The pyrolysis liquid was extracted with methyl isobutyl ketone, neutralized with a base, freeze-dried and extracted by ethyl acetate. The inventors claimed the method offered a way to obtain a highly pure crystalline form of levogucosan. However, this process seems to be very complex and is unlikely to be cost effective.

Thus, although some progress has been made, what is needed in the art are better, more robust methods with even better outcomes. Ideally, the method would be simple, use readily available inexpensive, and preferably non-toxic, ingredients, and produce a high purity of the desired product, thus obviating the need for extensive purification.

SUMMARY OF THE DISCLOSURE

Anhydrosugars, such as levoglucosan, are recognized as promising platform chemicals for the production of fuel and chemicals (e.g., biologically active compounds, surfactants and polymers). Most of their chemical applications require the use of nearly pure crystalline compounds. However, anhydrosugars are very difficult to synthesize in large quantities and without side products due to the nonselective nature of carbohydrate dehydration during pyrolysis (FIG. 2A). This leads to high production costs and currently limits the availability and use of anhydrosugar industrially.

People have studied anhydrosugar production since early 1900, but until now, have not provided any great improvements in this field because no one understands why the selectivity was low for anhydrosugar production on a molecular level.

In previous work, two approaches have been used to produce high purity anhydrosugars: (1) efficient isolation processes to recover pure anhydrosugar from a mix of side products, or (2) pretreating biomass with acid to remove inorganic salts, because inorganic salts were largely viewed as inhibitors for anhydrosugar production.

However, extensive purification steps and acid pretreatment are not effective enough to address the selectivity issue of anhydrosugar production. Thus, we studied the nonselective chemistry, and elaborated the criteria for pure anhydrosugar production.

We developed two approaches to enhance anhydrosugar selectivity: (1) protect the carbohydrate compounds before pyrolysis by forming an ether with the C1 anomer carbon (FIG. 2B); or (2) pretreat the carbohydrate substrate with metal salts and optional acid (FIG. 2C, shown with acid). Both of these approaches can effectively suppress the formation of undesirable side products.

Indeed, we have now shown that the nonselective chemistry of carbohydrate pyrolysis is substantially improved by alkoxy or aryloxy substitution at the anomeric carbon of glucose prior to thermal treatment. Through this "ex-situ ring-locking" step, we found that the selectivity to 1,6-anhydro-β-D-glucopyranose (levoglucosan, LGA) increased from 2% to greater than 90% after fast pyrolysis of the resulting sugar at 600° C. These results are unprecedented, and with further optimization of reaction conditions, we expect that even greater purity can be obtained (>93, 94, 95, 96, 97, 98, 99%). We refer to this method as a two-step method herein—ring locking followed by pyrolysis.

In a second method, we eliminated the initial ex-situ ring-locking step by using metal salts, and an optional acid, in the presence of deionized water (DI water). We refer to this method as a one-step method.

The mixture in both methods proceeds directly to flash pyrolysis or thin-film pyrolysis in a single step procedure. In all of the tests performed herein, a sufficiently thin film was used to eliminate temperature and concentration gradients during the lab-scale reaction. During the scale-up process, we intend to adopt this thin film idea because some of our tests show that "mass transfer" plays an important role on LGA selectivity, from an engineering perspective.

We thus provide several new methods of producing anhydrosugars with high purity from a carbon substrate, including:

An improved method of making an anhydrosugar by pyrolysis of a carbohydrate substrate to remove at least one water molecule thereby producing a desired anhydrosugar and side products, the improvement comprising 1) functionalizing the carbohydrate sugar at C1 position(s) before a heat treatment; or (2) pretreating the substrate sugar with a metal salt before a heat treatment, wherein lower amounts of said side products are produced by said improved method, as compared with a method that does not use (1) or (2).
Any method herein described, wherein said heat treatment occurs at about 350° C. to 600° C.
Any method herein described, wherein said heat treatment is performed on a solid sample, thus the sample is dehydrated before the heat treatment if needed.
Any method herein described, wherein said carbohydrate substrate is one or more of the following: mannose, galactose, allose, talose, glucose, sucrose, maltose, lactose, cellobiose, maltodextrins, starches, cellulose, cellulose byproducts, and derivatives thereof.
Any method herein described wherein said carbohydrate substrate is a polymeric sugar and where the method is preceded by a step converting said polymeric sugar to one or more simple sugars.
Any method herein described, wherein at least 25, 30, 40, 45, 50, 55, 60, 65, 70, 75, 80, 85, 90, or 95% of the desired anhydrosugar is produced.
Any method herein described, wherein the desired anhydrosugar is levoglucosan (C6H10O5), mannosan (C6H10O5), galactosan (C6H10O5), levoglucosone (C6H6O3) or 5-hydroxymethylfurfural (C6H6O3), furfural, 1,4;3,6-Dianhydroglucose, anhydroglucofuranose or combinations thereof.
A method of making an anhydrosugar, comprising:
contacting an amount of a carbohydrate substrate with an amount of a metal salt additive and optional acid in the presence of a liquid to form an first mixture; removing the liquid from the first mixture to form a solid mixture; and performing a heat treatment on the solid mixture to convert said substrate sugar to an anhydrosugar.
Any metal salt method herein described, wherein said removing step results in a thin film of said solid mixture.
Any metal salt method herein described, wherein pretreating the carbohydrate sugar with a metal salt before a heat treatment further comprises addition of an acid.
Any metal salt method herein described, wherein said metal salt comprises a cation chosen from groups 3-14 on the periodic table.
Any metal salt method herein described, said contacting step further includes an amount of an acid.
Any metal salt method herein described, wherein said acid is $H_2SO_4$, $H_3PO_4$, HCl, HI, HBr, or a transition metal Lewis acid.
Any metal salt method herein described, wherein said metal salt comprises a cation chosen from groups 1 and 2 on the period table.
Any metal salt method herein described, wherein said metal salt is KCl, $CaCl_2$, $MgCl_2$, $ScCl_3$, $VCl_3$, $Cr(II)Cl_2$, $Cr(III)Cl_3$, $MnCl_2$, $Fe(II)Cl_2$, $Fe(III)Cl_3$, $CoCl_2$, $NiCl_2$, $CuCl_2$, $ZnCl2$, $GaCl_3$, $AlCl_3$, $InCl_3$, $Sn(II)Cl_2$, $Sn(IV)Cl_4$ and combinations thereof.
A method of making an anhydrosugar, comprising:
dissolving a carbohydrate substrate in a solvent;
performing a Fischer glycosidation on the C1 carbon of said carbohydrate substrate by reacting said dissolved sugar substrate with an alcohol in the presence of a solid acid catalyst, wherein said Fischer glycosidation adds the alcohol on said C1 carbon as an ether; removing said solid acid catalyst and said solvent to form a solid sample; and, performing heat treatment on said solid sample to produce a desired anhydrosugar.
Any C1 blocking method herein described, wherein said alcohol is alkane or aryl based.
Any C1 blocking method herein described wherein said solid acid catalyst is Amberlyst-15.
Any C1 blocking method herein described wherein said ether has a methyl or phenyl group.
Any method as described herein, wherein the starting carbohydrate substrate is glucose, fructose, xylose, cellulose, hemicellulose, starch, arabinose, and any feedstock mentioned herein. Any method as described herein, wherein the starting carbohydrate substrate has a pentose or hexose ring. Any method described herein, wherein the pyrolysis heat treatment occurs at about 350° C. to 600° C. Any method described herein, wherein at least 25, 30, 40, 45, 50, 55, 60, 65, 70, 75, 80, 85, 90, 95% or more of the desired anhydrosugar is produced.

As used herein, "pyrolysis" and "heat treatment" are used interchangeable herein to refer to the use of heat to decompose or convert the starting organic matter to other matter. The resulting matter is referred to as "pyrolysis products". Any unreacted starting organic matter is simply referred to as "unreacted material".

There are three types of pyrolysis: slow pyrolysis, fast pyrolysis, and flash pyrolysis and they are differentiated based on both the heating rate and residence time. Residence time is the average time that the compound will remain in the reactor. It is obtained by dividing the reactor volume by the volumetric flow rate entering the reactor. "Slow pyrolysis" has a low heating rate (around 0.005° C. s$^{-1}$) and long residence time (minutes to days). "Fast pyrolysis" has a heating rate ranging between 5 to 100° C. s$^{-1}$ and a short residence time of 1 to 5 s.

"Flash pyrolysis", which was used herein, has the highest heating rate (up to 10$^{4}$° C. s$^{-1}$) and shortest residence time (<1 s). As a proof of concept, the methods disclosed herein used the highest heating rate 10$^{4}$° C. s$^{-1}$, and a residence time between 157 ms to 1244 ms. Preferably, the residence time is between 157 to 1000 ms, and most preferably, the residence time is 157 ms.

"Thin-film pyrolysis" involves heating a thin film (<10 μm) of the starting substrate. It can be combined with either slow, fast or flash pyrolysis. The present methods were evaluated using a 5150 Pyroprobe® analytical pyrolyzer (CDS Analytical Inc.), which involves the use of a small, open ended quart sample vial. Thus, a film is preferred because a chunk of solid sample would require use of a stopper (e.g. quartz wool) to prevent the solid sample from falling out or dislodging the sample vial.

To form the thin film, the sugar is first dissolve in deionized water or a deionized water-based solvent mixture (such as e.g. 1-propanol:H$_2$O in a 1:3 by volume ratio), then a small aliquot is deposited in the quartz sample vial. The deionized water or solvent is evaporated by any known method, leaving a film of sugar for pyrolysis.

The methods disclosed herein can use flash pyrolysis, thin-film pyrolysis or both together. Other pyrolysis or heat based conversion methods could also be used.

As used herein, "carbohydrate substrate" refers to the starting material and can include simple sugars (monosaccharides), disaccharides, as well as polymers thereof, such as starch and cellulose, and various derivatives or breakdown products of same. This includes cellulose byproducts that come from pulp-processing and naturally-occurring lignocellulose.

As used herein, "substituted" sugar or "C1-substituted sugar" refers to a sugar molecule that has been modified at the C1 hydroxyl group position to add a new moiety ("OR"). The C1 residue can also be referred to as "blocked" or "protected."

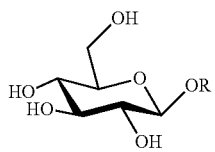

A methoxy substituted C1 (R=CH$_3$) glucose molecule is referred to herein as methyl glucoside, or "MG" and includes methyl-α-glucoside (α-MG) and methyl-β-glucoside (β-MG). A phenoxy substituted C1 (R=Ph) glucose is referred to herein as phenoxy glucoside, or "PG" includes phenyl-α-glucoside (α-PG) and phenyl-β-glucoside (β-PG). A "glycoside" is a molecule in which a sugar is bound to another functional group (e.g., alkoxy or aryloxy) via a glycosidic bond, and a glucoside is a glycoside derived from glucose. "G" is glucose, which includes α-glucose (α-G) and β-glucose (β-G).

We have found that levoglucosan (LGA) forms preferentially when the ring-opening of the glucose unit of the starting sugar substrate material is hindered by the presence of a substituent group other than a hydrogen or hydroxyl on the C1 carbon. The C1 carbon is an anomeric carbon, which is the hemiacetal or hemiketal carbon where there can be two different configurations in the cyclic sugar. It can either be α or β depending on the relative position of the —CH$_2$OH group and the —OH group on the anomeric carbon. α refers to the two groups being on opposite sides, and β refers to the two groups being on the same side.

The anomeric position is easily oxidized and can form glycosidic linkages readily. When synthesizing the substituted carbon substrates, the new moiety substitutes the hydroxyl group on C1 (—OH to —OR).

As used herein, "Fischer glycosidation" refers to a well-known chemical reaction wherein a glycoside is formed by the reaction of a sugar monomer (aldose or ketose) with an alcohol in the presence of an acid catalyst. Thus, the ex-situ ring-locking method described herein replaces the entire —OH group on the C1 carbon with an —OR, instead of merely substituting the hydroxyl hydrogen for an R group.

As used herein, "alkoxy" refers to R—O groups, wherein R is an alky group. "Aryloxy" refers to R—O groups where R is an aryl group and "phenoxy" refers to R—O groups where R is benzene (C$_6$H$_5$O—).

The "desired anhydrosugar" refers to the anhydrosugar(s) that is of interest to the user. Though the methods are exemplified by targeting the production of LGA, this is exemplary only and any anhydrosugar can be made using the disclosed methods.

As used herein, "metal salt" refers to ionic salts that comprising at least one metal cation. When dissolved in a solvent, typically aqueous based, the metal salt is purely ionic and its aqueous ions behave as a mixture of hydrated ions and molecular solvent. This behavior is distinct from an "ionic liquid" which is an organic salt that is liquid at room temperature, and a "molten salt," which is salt that becomes liquid at elevated temperatures (~100° C.). Both of these liquids consist of ions and ion pairs (dissociated molecules).

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, and the like.

The following abbreviations are used herein:

| ABBREVIATION | TERM |
|---|---|
| AGF | Anhydroglucofuranose |
| DGP | dianhydroglucopyranose |
| FF | Furfural |

-continued

| ABBREVIATION | TERM |
|---|---|
| G | glucose |
| Ga | galactose |
| HMFw | Hydroxymethylfurfural |
| LGA | levoglucosan |
| LGO | Levoglucosenone |
| Man | mannose |
| MF | methyl furfural |
| MG | Methyl glucoside |
| MGa | Methyl galactoside |
| MM | Methyl mannoside |
| PG | Phenyl glucoside |
| R | R is alkyl or aryl |

DETAILED DESCRIPTION

Figure 1:
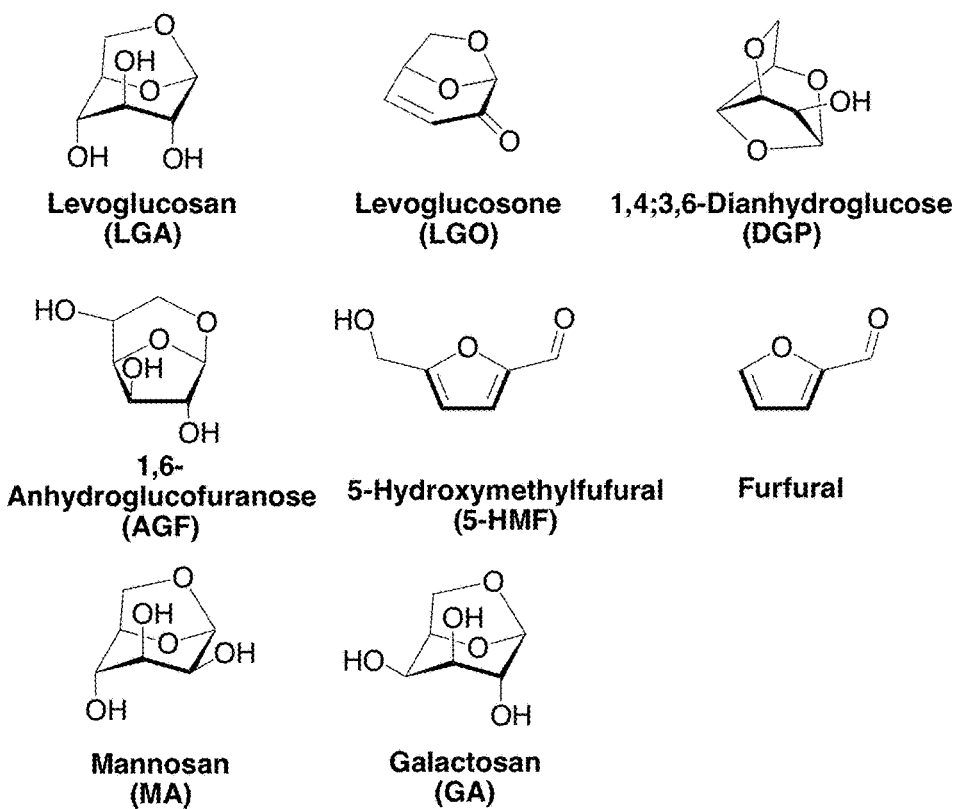
FIG. 1. Structure of anhydrosugars. Levoglucosan ($C_6H_{10}O_5$) is produced from glucose ($C_6H_{12}O_6$) by elimination of one water molecule. Mannosan ($C_6H_{10}O_5$) and galactosan ($C_6H_{10}O_5$) are producing from corresponding hexoses (mannose and galactose) by elimination of one water molecule. Levoglucosone ($C_6H_6O_3$) is produced from glucose by elimination of three waters. 5-hydroxymethylfurfural ($C_6H_6O_3$) is produced from fructose ($C_6H_{12}O_6$) or glucose ($C_6H_{12}O_6$) by elimination of three water molecules.
Figure 2A:
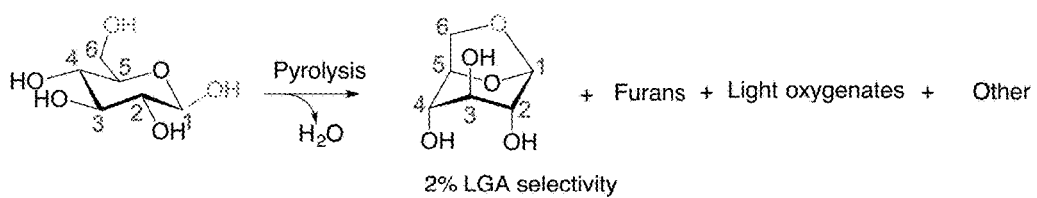
FIG. 2A-C. General schemes of sugar pyrolysis to form levoglucosan ("LGA", 1,6-anhydro-β-D-glucose). (A) Pyrolysis of β-D-glucose ("β-G") leads to LGA after elimination of one water molecule, among many other products formed. (B) Pyrolysis of functionalized β-G (alkyl glucoside) leads to LGA selectively after elimination of R—OH. (C) Metal salts and acid mediates glucose pyrolysis.
Figure 2B:
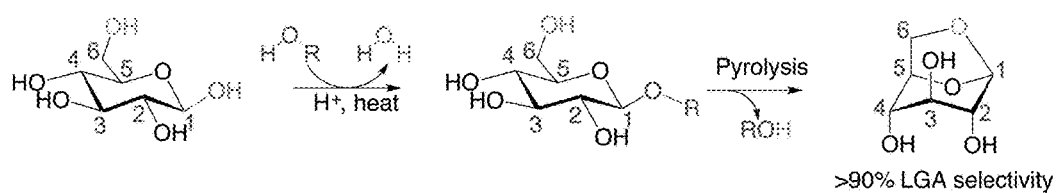
Figure 2C:
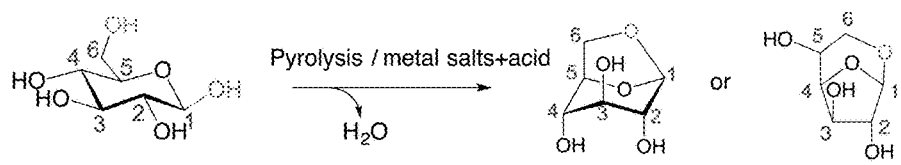

We describe herein two new methods of producing anhydrosugars with high purity from a carbohydrate substrate.

The first method is a two-step method wherein the first step is protecting the sugar substrate with an ex-situ ring-locking agent on the C1 anomeric carbon. By substituting the C1 hydroxyl (anomer carbon) with either an alkoxy or aryloxy group from an alcohol, the new ether functional group locks the sugar's 6-membered pyranose ring. This blocks many of the competing reaction pathways, including ring-opening pathways, making the reaction up to 90% selective for LGA.

To the extent that the carbohydrate substrate is a polymer, it may need to be converted to monomers first. This can be easily accomplished by acid hydrolysis, enzymatic hydrolysis, and the like. However, for the proof of concept work, we have used glucose and cellulose as starting materials.

Although the above ex-situ ring-locking and pyrolysis method is extremely efficient, a one-step method is preferred because it is even simpler to perform. The one-step method includes pyrolyzing a mixture of metal salt, plus or minus acid, to form the anhydrosugar.

In more detail, the one-step method requires (a) contacting an amount of the carbohydrate substrate with an amount of a salt additive, and optional acid, in the presence of a solvent to form an initial mixture; (b) optionally removing the solvent from the initial mixture to form a final solid mixture; (c) and performing heat treatment of either the initial mixture or the final solid mixture to form the anhydrosugar, which is more pure than prior art methods.

It is unclear if the increase in selectivity of LGA is the result of the salt's cation, anion or a synergistic effect with both ions. However, increased selectivity was seen with a variety of cation and anion combinations. We have also seen herein that the selectivity of LGA in the one-step method increases under acidic conditions for certain salt additives.

Variations on these methods include any of the following in any combination:

- Use of different substituent groups on C1 position (e.g., larger alkyl or aryl groups for R) of the carbohydrate substrate can enhance the selectivity of levoglucosan.
- Use a different starting carbohydrate substrate to obtain other value-added chemicals. For instance, different substituents on C1 of pentose can produce anhydrofuranose.
- The combination of chemical and thermal treatments approaches can not only be applied to glucose but also be applied on more complex carbohydrate substrates (e.g., cellulose).
- The combination of chemical and thermal treatments approaches can be applied on different aldohexose (e.g., mannose, galactose, allose, talose, etc.) for the corresponding anhydrosugar production.
- The concept of increasing the selectivity of levoglucosan can be scaled up to make industrial amounts of product.
- Instead of adding a functional group to a sugar substrate to act as an ex-situ ring-locking agent, direct pyrolysis of the glucose with metal salts, and optional acid, can also enhance the selectivity of levoglucosan. This strategy will be not only applicable for levoglucosan production, but also other value-added chemicals (e.g., levoglucosenone and hydroxymethylfurfural).

The present methods are exemplified with respect to the tests described below. However, these are exemplary only, and the methods can be broadly applied to any carbohydrate. The following examples are intended to be illustrative only, and not unduly limit the scope of the appended claims.

Pyrolysis Sample Preparation and Analysis Methods

In the following tests, samples were prepared by transferred into an open-end cylinder quartz tube (1.9×25 mm, diameter×length, CDS Analytical Inc., Oxford, Pa.) by microliter syringe (Hamilton 700 series, 10 μL), a small aliquot of the sample. Any solvent was removed by vacuum oven at 0.7 atm and 37° C. for 3 hours, resulting in thin film (32 μg) being formed on the inner surface of the quartz tube.

The quartz tubes were loaded into a 5150 Pyroprobe® analytical pyrolyzer (CDS Analytical Inc.) that was attached to an Agilent 6890N GC/FID (Santa Clara, Calif.). The Pyroprobe was rapidly heated to 600° C. (flash pyrolysis ramp rate of ~20,000° C./s, heating time<1 s), where it was held it for 20 s. The gas-phase effluent of pyrolysis products was then analyzed by GC/FID.

Pyrolysis Data Evaluation

In the following tests, glucose pyrolysis was taken as a benchmark carbohydrate in evaluating both disclosed methods and the target value-added chemical was levoglucosan (LGA). In order to monitor the pyrolysis-product distribution of the glucose moiety, the yields are reported in terms of molar carbon yield, where the moles of carbon in the product are divided by the moles of carbon in the glucose moiety. The reported LGA selectivity is defined as the LGA carbon yield in ratio to the conversion of the reactant (carbohydrate).

The following equations are used to calculate carbon yield of LGA (Y), conversion rates of different substrates (X) and selectivity to LGA (S).

Equation 1 provides the LGA carbon yield ($Y_{LGA}$) for substituted glucose, but can also be used to calculate the LGA carbon yield ($Y_{LGA}$) for glucose.

$$Y_{LGA} = \frac{\text{moles of carbon in detected } LGA}{\text{initial moles of carbon in glucose moiety}} \times 100\% \quad \text{Equation 1}$$

$$= \frac{6 \times (\text{moles of detected } LGA)}{6 \times \text{initial moles of substituted glucose}} \times 100\%$$

$$= \frac{\text{moles of detected } LGA}{\text{initial moles of substituted glucose}} \times 100\%$$

Equation 2 provides for the conversion rate ($X_G$) for glucose.

$$X_G = \frac{\text{initial moles of glucose} - \text{moles of } HPLC \text{ detected glucose residue}}{\text{initial moles of glucose}} \times 100\% \quad \text{Equation 2}$$

$$= \left(1 - \frac{\text{moles of } HPLC \text{ detected glucose residue}}{\text{initial moles of glucose}}\right) \times 100\%$$

Methanol and phenol were used as in situ generated internal standards to quantify glucoside conversion rates of methyl-substituted glucose (MG) and phenyl-substituted glucose (PG), respectively. Thus, Equation 3 provides the conversion rate for methyl substituted glucoside ($X_{MG}$) for methyl β-glucoside and methyl α-glucoside as a function of the detected methanol. The conversion rates of phenyl substituted glucoside ($X_{PG}$) for phenyl β-glucoside and phenyl α-glucoside as a function of detected phenol is provided in Equation 4.

$$X_{MG} = \frac{\text{moles of reacted } MG}{\text{initial moles of } MG} \times 100\% \quad \text{Equation 3}$$

$$= \frac{\text{moles of detected methanol}}{\text{initial moles of } MG} \times 100\%$$

$$X_{PG} = \frac{\text{moles of reacted } PG}{\text{initial moles of } PG} \times 100\% \quad \text{Equation 4}$$

$$= \frac{\text{moles of detected phenol}}{\text{initial moles of } PG} \times 100\%$$

For Equations 3 and 4, we confirmed that (i) methanol/phenol is thermally stable under pyrolysis conditions (no side reaction); (ii) methanol/phenol does not react with other pyrolysis products to form ethers; (iii) pyrolysis products do not further decompose to methanol/phenol, which means methyl-glucoside/phenyl-glucoside should be the only source to produce methanol/phenol.

The LGA yield, conversion of starting precursor ($X_i$, wherein i=G, MG, or PG), and selectivity to LGA ($S_{LGA}$) are related per Equation 5.

$$S_{LGA} \times X_i = Y_{LGA} \times 100\% \quad \text{Equation 5}$$

Equations 6-8 shows the calculation of $S_{LGA}$ when i=MG, PG and G.

$$S_{LGA} = \frac{\frac{\text{moles of detected } LGA}{\text{initial moles of } MG}}{\frac{\text{moles of detected methanol}}{\text{initial moles of } MG}} \times 100\% \quad \text{Equation 6}$$

$$= \frac{\text{moles of detected } LGA}{\text{moles of detected methanol}} \times 100\%$$

$$S_{LGA} = \frac{\frac{\text{moles of detected } LGA}{\text{initial moles of } PG}}{\frac{\text{moles of detected phenol}}{\text{initial moles of } PG}} \times 100\% \quad \text{Equation 7}$$

$$= \frac{\text{moles of detected } LGA}{\text{moles of detected phenol}} \times 100\%$$

$$S_{LGA} = \frac{\frac{\text{moles of detected } LGA}{\text{initial Moles of glucos}}}{\frac{\text{initial moles of glucose} - \text{moles of } HPLC \text{ detected glucose residue}}{\text{initial moles of glucose}}} \times 100\% \quad \text{Equation 8}$$

$$= \frac{\text{moles of detected } LGA}{\text{initial moles of glucose} - \text{moles of } HPLC \text{ detected glucose residue}} \times 100\%$$

Modifications to Equations 1-8 can easily be made for any starting carbohydrate substrate and/or target anhydrosugar.

Test 1: Alpha- and Beta-MG

As an initial test, the pyrolysis of high-purity methyl substituted glucose, methyl-β-D-glucoside (β-MG") and methyl-α-D-glucoside ("α-MG"), were carried out. Methyl-α-D-glucoside (>99%) and methyl-β-D-glucoside (>99%) were purchased from Sigma Aldrich (St. Louis, Mo.). β-D-glucose (β-G") (>80.0%, containing α-D-glucose) was purchased from TCI America (Montgomery, Pa.). β-MG, α-MG and β-G were dissolved into deionized water (18.2 MΩ, Barnstead Nano-pure Diamond System) and 4 µL of the solution (8 mg/ml) was transferred into an open-end cylinder quartz tube per the sample preparations and analysis methods described above.

Both of the methyl substituted D-glucosides produced LGA more selectively than β-G. However, under the same pyrolysis experimental conditions, the sugar compounds were found to undergo different extents of reaction and volatilization.

Figure 3:
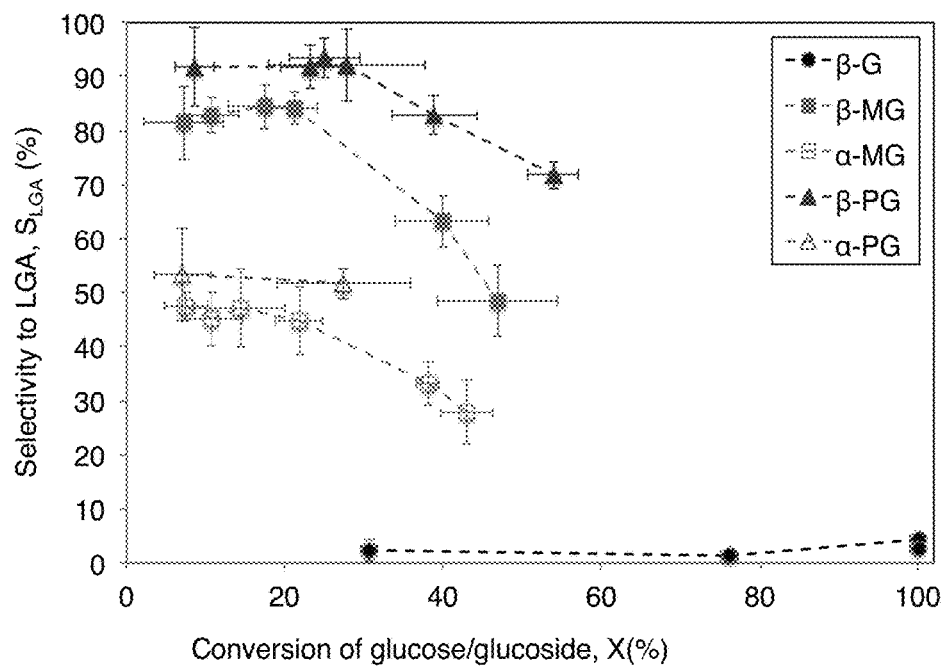
FIG. 3. LGA carbon selectivity-conversion analysis for the different sugar compounds. Each data point represents a minimum of 3 experiments, and the error bar is ±1 standard deviation. Conversion of the substituted sugars is adjusted by control of carrier gas space velocity and sample heating time. Heating times between 0.1 and 20 sec (at a 100:1 split ratio) achieved conversions of <20%, and GC split ratios between 100:1 and 10:1 (at a heating time of 20 sec) achieved conversions of >20%. Flash pyrolysis reaction conditions: 600° C., thin-film sample size=32 μg, film thickness<10 μm.

The conversion rate (X) for β-G, β-MG and α-MG was 100%, 17%, and 15%, respectively. To compare the relative reactivities of the various compounds, we measured LGA yields ($Y_{LGA}$) at different substrate conversions ($X_i$), from which we then calculated LGA selectivity values $S_{LGA}$ (=$Y_{LGA} \div X_i$). Further, conversion rates were adjusted by controlling the space velocity and probe heating time: when conversion rates were less than 20%, we controlled the conversion by increasing the heating time from 0.1 sec to 20 sec. But, when the conversion rate is larger than 20%, we controlled the conversion by decreasing the GC split ratio from 100:1 to 10:1 and keeping the heating time at 20 sec.

β-G presented very low selectivity to LGA (1-4%) at all conversion rates while the MGs showed significantly higher LGA selectivities across a wide range of conversion rates (FIG. 3). In particular, β-MG showed very high selectivity towards LGA (~84%) as compared to β-G (~3%) when the conversion rate was less than 20%. As β-MG conversion rates increased up to 47%, the LGA selectivity decreased to 48% because of the formation of a new set of pyrolysis products, such as furan derivatives and light oxygenates, at the expense of LGA. Thus, in a conversion range of 0-47%, the major pyrolysis product peaks from the β-MG pyrolysis are still methanol, LGA and unreacted β-MG.

α-MG pyrolysis showed a similar trend to β-MG, but the selectivity was roughly half as much. This indicates that the LGA forms more easily when the C1 methoxy and C6 hydroxymethyl groups are on the same side of the ring structure (as is the case for the β anomer).

Qualitatively, the pyrolysis of β-G produced the most char, whereas both MGs produced trace amount of char (barely visible). Further, as the conversion increased, the char amount increased. The char is indicative of the difference in purity of the samples, as the purchased MGs had a higher purity.

Test 2: Alpha- and Beta-PG

Different substituent groups (R) have also been tested in both the alpha and beta configurations. Phenyl-β-D-glucoside (97%) was purchased from Sigma Aldrich (St. Louis, Mo.), and phenyl-α-D-glucoside (>97%) was purchased from TCI America. Due to solubility issues, phenyl-β-D-glucoside and phenyl-α-D-glucoside were dissolved into 1-propanol:$H_2O$ (1:3 by volume) solvent mixture. A 4 µL aliquot of the solution (~8 mg/mL) was transferred into an open-end cylinder quartz tube per the sample preparations and analysis methods described above.

As expected, the pyrolysis of the phenylated glucosides ("α-PG" and "β-PG") gave very similar trends as methylated glucoside. However, an even higher LGA selectivity (up to 93% selectivity to LGA, FIG. 3) was seen with the phenylated glucosides, suggesting that the larger blocking group was more protective.

The substitution of the C1 hydroxyl with a methyl or phenyl improved the selectivity of LGA over a substituted C1 at all conversion rates. At the similar conversion, LGA selectivity following: β-PG>β-MG>α-PG>α-MG>β-G. Thus, giving credence to the hypothesis that substitution at this carbon provides an "ex-situ ring-locking" mechanism during the pyrolysis step.

Test 3: Synthesized MG

We next synthesized a substituted sugar by replacing the C1 hydroxyl group of β-D-glucose ("β-G") with a methoxy group. The synthesis experiments were carried out in a microwave reactor (Anton Paar Monowave 300), adapted from the established procedure in Yang, Abu-Omar, and Hu 2012.

In the synthesis, 90 mg of glucose, 21.5 mg of Amberlyst 15 (dry) and 2 ml of methanol were added to a 30 mL reaction tube and heated to 130° C. The temperature was held there for 30 minutes while being stirred at 1200 rpm. After completion of the reaction and the subsequent cooling, the solution of reaction products was diluted to 10 mL using DI-water, and the solid catalyst (Amberlyst 15) was filtered using a syringe filter.

The remaining filtrate contained crude methyl-glucoside, which was then analyzed by High Performance Liquid Chromatography (HPLC). 4 µL of the filtrate was transferred into an open-end cylinder quartz tube per the sample preparations and analysis methods described above.

The synthesized product (filtrate) contained 84 wt % methyl-D-glucoside ("MG"), of which 44% was the β anomeric form (β-MG). The LGA selectivity from the pyrolysis of this crude MG was ~64%. This, again, was significantly higher than the experimentally determined ~2% selectivity from purified β-G.

Test 4: Other Substrates

The method can also be applied to more complex substrates. Three different cellulose sources (cellulose, filter paper and cotton) were converted to methyl-glucoside. The synthesis experiments were carried out with cellulose (the average degree of polymerization was 133, reported by Mettler et al. 2012), Whatman filter paper (grade 42) and sterile absorbent cotton (USP grade, U.S. cotton). These substrates were pre-washed to remove mineral contaminants (Patwardhan et al. 2009), wherein 1 g of the substrate was washed by 20 mL of $HNO_3$ (0.1 N) for 5 minutes while stirring, filtered, and final, washed with 60 mL DI-water.

We applied the same protocol that was used to synthesize the crude methyl-glucoside from glucose in Test 3, but the yields of the crude methyl-glucosides were very low due to the lower reactivity of these polymeric substrates. In order to enhance the methyl-glucoside yield, the reactions were performed using a stainless tube reactor at reasonable higher temperature (~210° C.) (Deng et al. 2010). In a typical synthesis procedure, 100 mg of pre-washed and grinded substrate biomass, and 10 mg Amberlyst-15 catalyst was suspended into 4 mL methanol. The solution mixture was added to a 16 mL stainless steel reactor and the reactor was placed in a preheated oven at 210° C. for 30 min.

After the reaction, the reactor was cooled immediately and quickly by ice bath to quench further reaction. The solid catalyst (Amberlyst-15) and unreacted substrate biomass was filtered using a syringe filter and dried in an oven at 110° C. for 1 hr before being weighted to calculate the conversion of substrate biomass.

The filtrate was concentrated to 6 mL, and analyzed by HPLC. 20 µL of the filtrate was transferred into a quartz tube and dried under vacuum to form the crude methyl-glucoside thin-film. The same pyrolysis and GC/FID settings as above were used.

Figure 4:
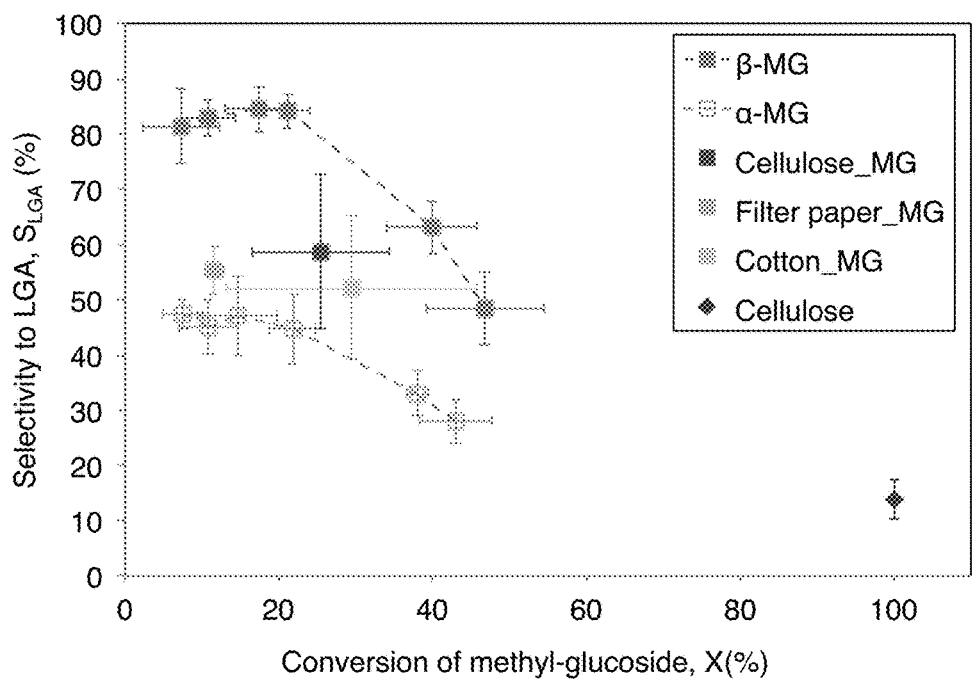
FIG. 4. Levoglucosan produced from various cellulose sources.

The results from this test are shown in Table 1 and FIG. 4. The resulting crude MG derived from cellulose ("Cellulose_MG"), filter paper ("Filter_paper_MG") and cotton ("Cotton_MG) contained 32%-39% methyl-glucoside. Flash pyrolysis of the various crudes resulted in LGA yields of 7-16% and LGA selectivities of 52-60% (see also FIG. 4).

TABLE 1

Crude MG synthesis and pyrolysis results

| | Crude MG synthesis | | | | | | Crude MG pyrolysis | |
|---|---|---|---|---|---|---|---|---|
| | | | | Crude MG composition | | | | MG |
| Substrate | Substrate convers'n (wt %) | α-MG yield (wt %) | β-MG yield (wt %) | α-MG (wt %) | β-MG (wt %) | Impurity (wt %) | LGA selectivity (%) | pyrolysis convers'n (%) |
| Cellulose | 24 ± 4 | 6 ± 0.6 | 4 ± 0.4 | 23 ± 4 | 15 ± 3 | 62 | 59 ± 14 | 25 ± 9 |
| Filter paper | 22 ± 7 | 4 ± 0.2 | 3 ± 0.1 | 24 ± 6 | 16 ± 4 | 61 | 55 ± 4 | 12 ± 1 |
| Cotton | 20 ± 4 | 4 ± 0.5 | 2 ± 0.4 | 20 ± 2 | 13 ± 1 | 68 | 52 ± 13 | 30 ± 16 |

Test 5: Other Aldohexoses

The two-step ex-situ ring locking method can also be applied to other aldohexose structures as well, e.g., mannose, galactose, allose, talose, etc. This is exemplified through the use of purified mannose and galactose as starting materials. D-Mannose and D-galactose are common stereoisomers of D-glucose.

Methyl α-D-mannopyranoside (>99% GC) and methyl α-D-galactopyranoside were purchased from Sigma Aldrich. Sample preparation procedures and pyrolysis conditions are exactly same as Test 1.

Figure 5:
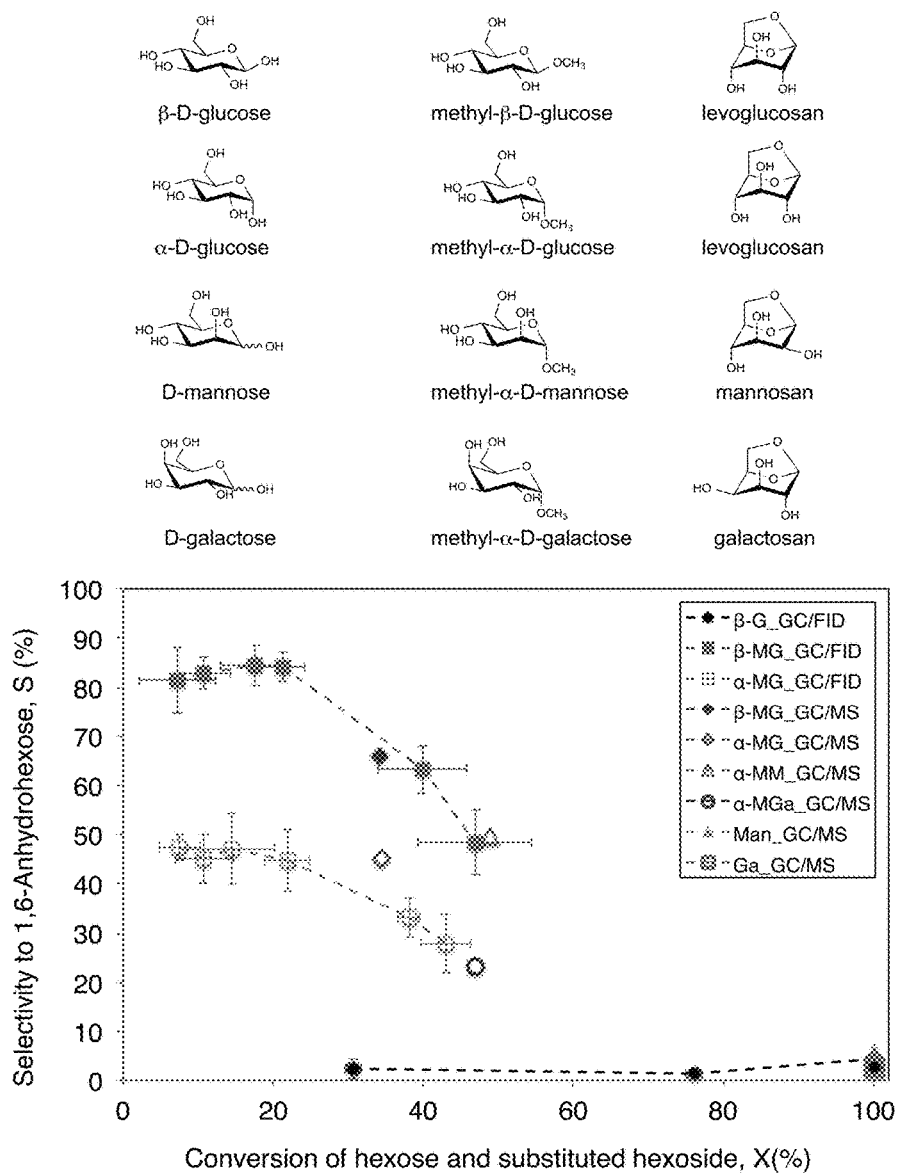
FIG. 5. 1,6-anhydrohexoses produced from pyrolysis of methyl hexosides and the selectivity and yield values for the corresponding 1,6-anhydrohexoses. Note: Methyl-α-D-mannoside ("α-MM"); Methyl-α-D-galactoside ("α-MGa"); D-Mannose ("Man"); D-Galactose ("Ga").

As shown in FIG. 5, the selectivity and yield values for the corresponding 1,6-anhydrohexoses mannosan (MM) and galactosan (Ga) were much higher for methyl-α-mannoside ("α-MM") (50% and 23%) and methyl-α-galactoside ("α-Ga") (23% and 11%) compared to α/β-mannose ("Man") (5% and 5%) and α/β-galactose ("Ga") (2% and 2%).

Test 6: One-Step Conversion

The intention in Tests 1-5 was to improve anhydrosugar, such as levoglucosan (LGA), selectivity by using alkoxy or phenoxy functional groups to replace the hydroxyl group at the anomeric carbon of sugar prior to thermal treatment. These tests used a two-step process, wherein the first step was the "ex-situ ring-locking" step. Through this ex-situ ring-locking step, we found that the selectivity to anhydrosugar increased drastically.

Based on our excellent results from the two-step process, we developed a one-step process by mixing sugar, metal salt, and an optional acid, and directly applied thermal treatment to the resulting mixture. As above, the sugar, metal salt, and an optional acid are dissolved in a solvent, then a small aliquot is placed in a pyrolysis tube to form a thin film after the solvent is evaporated. However, the sugar is not ring-locked until the thermal treatment. Thus, the one-step refers to the in-situ ring-locking and conversion that occurs during the heat treatment.

Salts have previously been used in carbohydrate conversion. US20100317879 describes a process for carbohydrate into 5-hydroxymethylfurfural (5-HMF) wherein the carbohydrate is dissolved into an ionic liquid and heated. The ionic liquid can also contain a metal halide as a catalyst. However not all metal halides work, particularly $LaCl_3$, $MnCl_2$, NaCl, and LiCl. Further, when glucose was used as the substrate, only $CrCl_2$ and $CrCl_3$ improved anyhydrosugar production. The disadvantages of US20100317879 are the expense of using ionic liquids and the lack of other value-added materials being produced in useable quantities.

$ZnCl_2$ impregnated biomass was also used to produce furfural (FF) using low-temperature fast pyrolysis (Lu 2011). However, the presence of this salt inhibited the formation of LG and hydroxyacetaldehyde (HAA); and, LGO, LAC, and DGP were only produced when low concentrations of $ZnCl_2$ were used. Further, the LGO, LAC, and DGP were converted to FF at temperatures above 400° C.

However, none of these methods were able to increase the production of LGA. Further, the production of other anhydrosugars required expensive chemicals (liquid salts), additional steps (impregnation step for $ZnCl_2$) or carefully heating (i.e. the conversion of anhydrosugars to FF at temperatures above 400° C. in Lu 2011). Thus, we decided to build off of the two-step method above and heat a metal salt/carbohydrate mixture.

Figure 6:
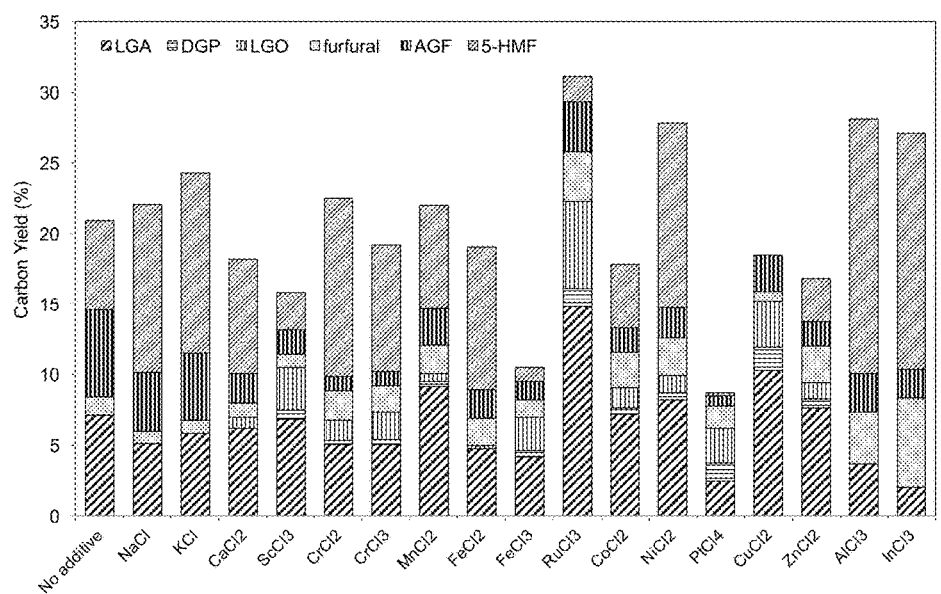
FIG. 6. Metal salts (5 mol percent based on glucose) mediated glucose pyrolysis. Condition: temperature=350° C., holding time=60 sec.

When using just a metal salt, we observed an increase in the selectivity of LGA for salts containing a transition or post-transition metal cation. FIG. 6 displays the anhydrosugar production for a few of the metal salts. Overall, the improved LGA production was seen with metal salts in the first row transitional metals (Ti, V and Ga not tested due to their reactivity with water) and post-transition metals salts including Al, In, Sn, and Ga. However, other salts, such as $NiCl_2$, $AlCl_3$ and $InCl_3$ also produced higher amounts of 5-HMF, LGO ($RuCl_3$) and/or DGP ($CuCl_2$).

The selectivity and conversion rate were even higher for transition metal salts when they were also Lewis acids (see e.g. $Fe^{3+}$, $Cu^{2+}$ and $Ru^{3+}$).

However, metal salts using Group 1 and 2 metal cations (alkali metals and alkaline earth metals) did not produce similar results. To improve their ability to increase anhydrosugar selectivity, we mixed these metal salts with an acid. We named this one-step process the "in-situ ring-locking" because the acid is the catalyst responsible for the dehydration, and we believe the metal salt will complex with carbohydrate for the ring-locking.

The carbon source (e.g., substrate) was mixed with an amount of metal salt additive (including, but are not limited to, $Li_2SO_4$, $Na_2SO_4$, $K_2SO_4$, $Cs_2SO_4$, $MgSO_4$, $CaSO_4$, etc.) and an amount of acid (e.g., $H_2SO_4$) in the presence of DI water to form an initial mixture. Greater than 80% of the DI water from the initial mixture was evaporated to form a final sample film. We then performed the heat treatment of the sample film at various temperatures (about 350° C. to 600° C.).

Similar increases in selectivity of anydrosugars are expected for the combination of metal salts having transitional metal cations with acid, too.

The metal salts above are exemplary only and are not intended to limited the choice of anions for the metal salt. For instance, $SO_4^{2-}$ anions in the salt were used to match the anions in the acid. But, we have found that salts comprising $Cl^-$ also improve LGA production. The other halides, $I^-$ and $Br^-$, are also acceptable anions. Similar results are expected with other anions.

Further, both strong and weak acids can be used. Both $NaHSO_4$ (a weak acid) and $H_2SO_4$ (a strong acid) were tested and produced increases in LGA production. The pH range for the initial mixture is 2-4 and can be used as guidance when selecting the acid. However, the heat treatment is applied to a thin film so pH is not an issue at that point.

Figure 7:
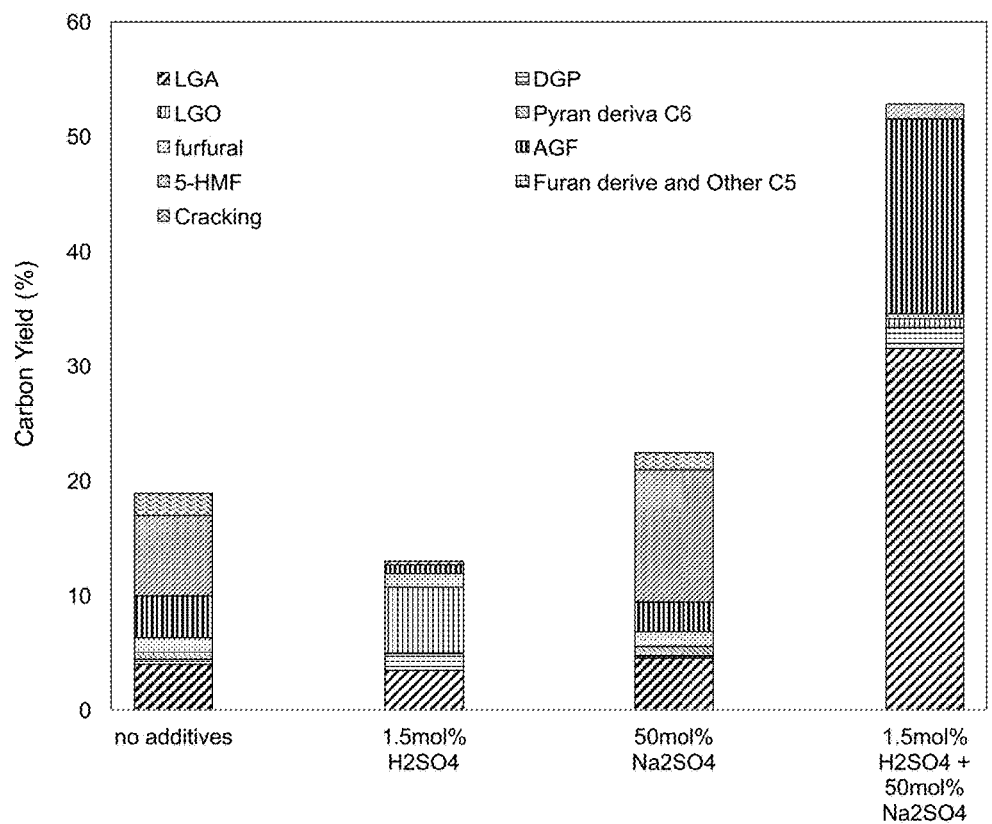
FIG. 7. Glucose dehydration catalyzed by sulfuric acid (2 mol % based on glucose) alone, or in combination with $Na_2SO_4$ (50 mol % based on glucose). Conditions: pyrolysis temperature=350° C., holding time=60 sec.

As shown in FIG. 7, neither $H_2SO_4$ nor $Na_2SO_4$ alone can enhance anhydrosugar production significantly, but the combination of $H_2SO_4$ and $Na_2SO_4$ did increase the yield of levoglucosan (LGA) and anhydroglucofuranose (AGF) significantly from 4% and 4% to 22% and 15%, respectively. Tests were performed with $Na_2SO_4$ loading ranges between 0 to 200 mole percent and $H_2SO_4$ loading ranges between 0 to 20 mole percent. We found that the loading of $H_2SO_4$ should be around 1 mole percent and the loading of $Na_2SO_4$ should be at least 10 mole percent, although these amounts may be further optimized. This difference is loading is thought to be the result of the acid working as a catalyst. Thus, only a small amount of acid needs to be added to the system, whereas the metal salt is more of an additive or reagent that should be in a larger quantity.

Figure 8:
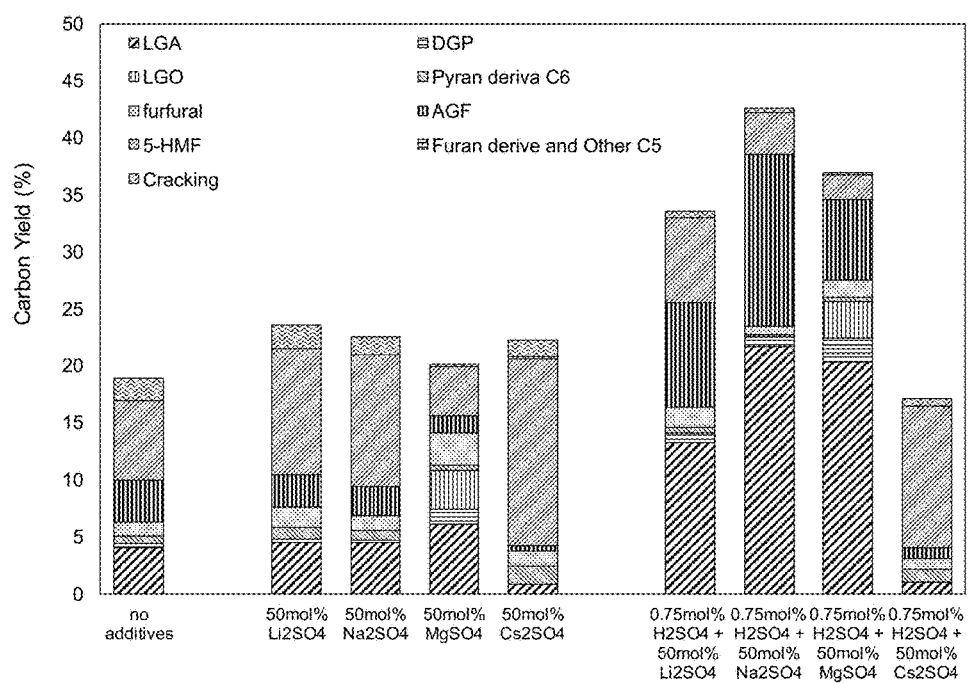
FIG. 8. Glucose dehydration mediated by various metal salts. Conditions: pyrolysis temperature=350° C., holding time=60 sec.

We also explored other salts and the results are shown in FIG. 8. Among all of the salts we tried, the combination of $Na_2SO_4$ and $H_2SO_4$ gave the best results, however, other metal salts were viable alternatives, especially magnesium.

The improvement of anhydrosugar yield was unexpected because:
- It has previously been reported in the literature that alkali or alkaline earth metal salt decrease the anhydrosugar yield and suggest the removal of these salts. U.S. Pat. No. 5,395,455, for instance, removes alkali and alkaline earth cations from the biomass (i.e. substrate) to allow an enhanced conversion of the cellulose and hemicellulose fractions to various anhydrosugars or sugars in a fast thermal pyrolysis process.
- Transition metal salts such as $ZnCl_2$ showed preferential production of anhydrosugars other than our targeted LGA.
- Acid is known to enhance anhydrosugar yield, but only in an uncontrollable manner.

In spite of such contrary teachings, we have found that the combination of the alkali or alkaline earth metal salts and acid actually enhance production of anhydrosugars, especially LGA, in a very controllable manner!

Figure 9A:
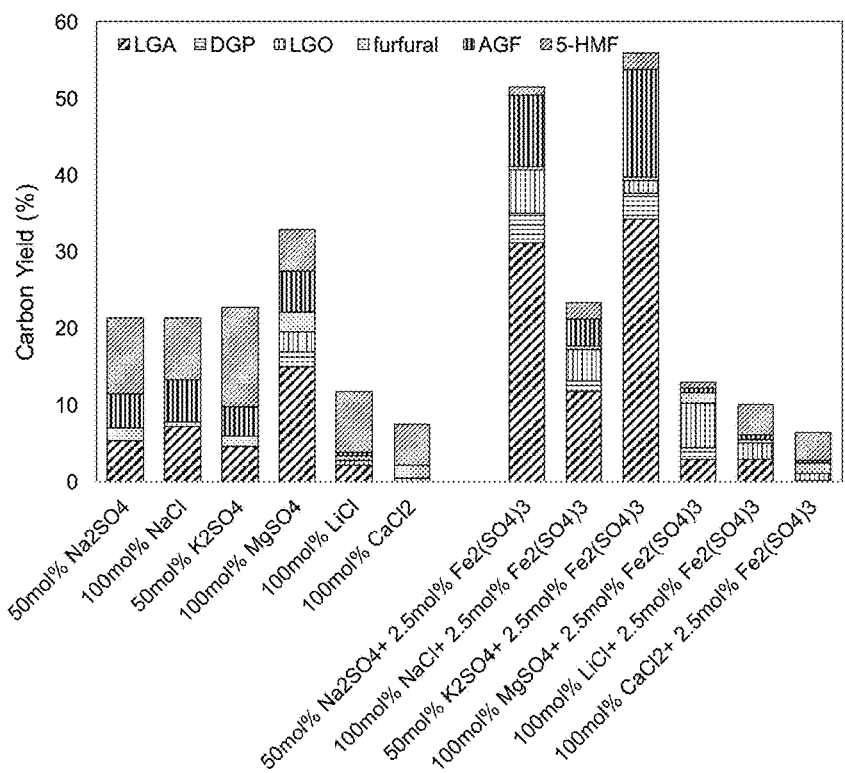
FIG. 9A-B. Glucose dehydration catalyzed by a transition metal Lewis acid salt (2.5 mol % based on glucose) and various alkali metals and alkaline earth metals salts (FIG. 9A) and $CuSO_4$ (FIG. 9B). Conditions: pyrolysis temperature=350° C., holding time=60 sec.
Figure 9B:
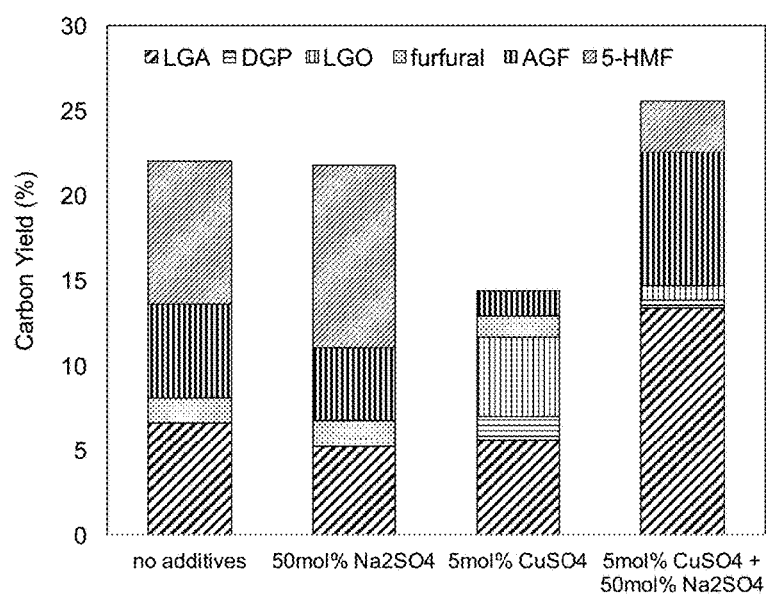

Since the combination of Bronsted acid and metal salts works, we also explored the combination of Lewis acid and metal salts. We used a transition metal Lewis acid, $Fe_2(SO_4)_3$, with various alkali and alkaline earth metal salts. The results are shown in FIG. 9A-B.

This combination showed a similar trend to the $Na_2SO_4$/$H_2SO_4$ and increased the production of anhydrosugars when compared to the use of only alkali and alkaline earth metal salts. Here, the selectively for LGA was the highest with potassium, instead of sodium and magnesium; however, magnesium showed high selectivity for the production of LGO, while Li and Ca showed improved selectivity of 5-HMF. Thus, the metal salt used in the conversion can be selected based on the target anhydrosugar composition. Further, differences were seen between sodium salts containing different anions. Thus, different salts complex with sugars in different ways, and have different preferences for the oxygen in sugar. This flexibility will allow a user to tune the conversion products based on their needs and the metal salts available to them.

Future work will involve testing a large number of metal salts and acid combinations to further define the best combinations for industrial use. However, these proof of concept experiments demonstrate broad applicability to metal salt with or without acid combinations.

The following references are incorporated by reference in their entirety for all purposes:

Czernik, S, and A V Bridgwater. 2004. "Overview of Applications of Biomass Fast Pyrolysis Oil." *Energy & Fuels,* 590-98. http://pubs.acs.org/doi/abs/10.1021/ef034067u.

Deng, Weiping, Mi Liu, Qinghong Zhang, Xuesong Tan, and Ye Wang. 2010. "Acid-Catalysed Direct Transformation of Cellulose into Methyl Glucosides in Methanol at Moderate Temperatures." *Chemical Communications* (Cambridge, England) 46 (15): 2668-70. doi:10.1039/b925723c.

Mettler, Matthew S., Samir H. Mushrif, Alex D. Paulsen, Ashay D. Javadekar, Dionisios G. Vlachos, and Paul J. Dauenhauer. 2012. "Revealing Pyrolysis Chemistry for Biofuels Production: Conversion of Cellulose to Furans and Small Oxygenates." *Energy & Environmental Science* 5 (1): 5414. doi:10.1039/c1ee02743c.

Patwardhan, Pushkaraj R., Justinus a. Satrio, Robert C. Brown, and Brent H. Shanks. 2009. "Product Distribution from Fast Pyrolysis of Glucose-Based Carbohydrates." *Journal of Analytical and Applied Pyrolysis* 86 (2): 323-30. doi:10.1016/j.jaap.2009.08.007.

Radlein, D. 2002. "Study of Levoglucosan Production—A Review." In *Fast Pyrolysis of Biomass: A Handbook*, edited by A V Bridgwater, 205-41.

Yang, Yu, Mandi M. Abu-Omar, and Changwei Hu. 2012. "Heteropolyacid Catalyzed Conversion of Fructose, Sucrose, and Inulin to 5-Ethoxymethylfurfural, a Liquid Biofuel Candidate." *Applied Energy* 99 (November): 80-84. doi:10.1016/j.apenergy.2012.04.049.

Lu, Qiang et. al. 2011 "Selective fast pyrolysis of biomass impregnated with $ZnCl_2$ to produce furfural: Analytical Py-Gc/MS study", *Journal of Analytical and Applied Pyrolysis* 90: 204-212.

U.S. Pat. No. 1,437,615
U.S. Pat. No. 3,309,356
U.S. Pat. No. 3,374,222
U.S. Pat. No. 3,235,541
U.S. Pat. No. 5,395,455
U.S. Pat. No. 5,023,330
U.S. Pat. No. 5,371,212
U.S. Pat. No. 5,432,276
US20100317879

The invention claimed is:

1. A method of making an anhydrosugar, comprising:
   a) dissolving a carbohydrate substrate in a solvent;
   b) performing a Fischer glycosidation on the C1 carbon of said carbohydrate substrate by reacting said dissolved sugar substrate with an alcohol in the presence of a solid acid catalyst, wherein said Fischer glycosidation adds the alcohol on said C1 carbon as an ether;
   c) removing said solid acid catalyst and said solvent to form a solid sample; and, d) performing heat treatment on said solid sample to produce a desired anhydrosugar.

2. The method of claim 1, wherein said heat treatment occurs at about 350° C. to 600° C.

3. The method of claim 1, wherein said alcohol is alkane or aryl based.

4. The method of claim 1, wherein said solid acid catalyst is Amberlyst-15.

5. The method of claim 1, wherein said ether has a methyl or phenyl group.

6. The method of claim 1, wherein said carbohydrate substrate is one or more of the following: mannose, galactose, allose, talose, glucose, pentose, hexose, sucrose, maltose, lactose, cellobiose, maltodextrins, starches, cellulose, lignocellulose, and derivatives thereof.

7. The method of claim 1, wherein said carbohydrate substrate is a polymeric sugar and where the method is preceded by a step converting said polymeric sugar to one or more simple sugars.

8. The method of claim 1, wherein the desired anhydrosugar is levoglucosan ($C_6H_{10}O_5$), mannosan ($C_6H_{10}O_5$), galactosan ($C_6H_{10}O_5$), levoglucosone ($C_6H_6O_3$) or 5-hydroxymethylfurfural ($C_6H_6O_3$), furfural, 1,4;3,6-Dianhydroglucose, anhydroglucofuranose or combinations thereof.

* * * * *